United States Patent [19]

Csom et al.

[11] 4,081,683
[45] Mar. 28, 1978

[54] MEASURING THE CONCENTRATION OF BORON IN WATER

[75] Inventors: Gyula Csom; Sandor Desi; Eva Szolnay, all of Budapest; Csaba Gyurkocza, Etyek; Imre Szucs, Budapest; Vilmos Varbiro, Budapest; Sandor Elo, Budapest; Sandor Benedek, Budapest, all of Hungary

[73] Assignee: Budapesti Muszaki Egyetem, Budapest, Hungary

[21] Appl. No.: 724,841

[22] Filed: Sep. 20, 1976

Related U.S. Application Data

[63] Continuation-in-part of Ser. No. 520,143, Nov. 1, 1974, abandoned.

[30] Foreign Application Priority Data

Nov. 5, 1973 Hungary .............................. BU 697

[51] Int. Cl.² ............................................. G01T 1/20
[52] U.S. Cl. ..................................... 250/364; 250/390
[58] Field of Search .............................. 250/390, 364

[56] References Cited
U.S. PATENT DOCUMENTS 3,009,062   11/1961   Brooksbank et al. ................ 250/364

Primary Examiner—Harold A. Dixon
Attorney, Agent, or Firm—Young & Thompson

[57] ABSTRACT

The concentration of boron dissolved in water is determined by positioning a measuring vessel between a radio-active neutron source and a neutron detector. The neutron source is disposed in a moderator and the detector is disposed in a relfector; while the test specimen, e.g. boric acid, is disposed between two flat parallel plates perpendicular to the path between the source and the detector. The time necessary for the detector to receive a certain number of neutrons varies linearly as the concentration of boron; and so the boron concentration can be displayed as a function of elapsed time in excess of that time necessary for the predetermined number of neutrons to be received through pure water.

1 Claim, 2 Drawing Figures

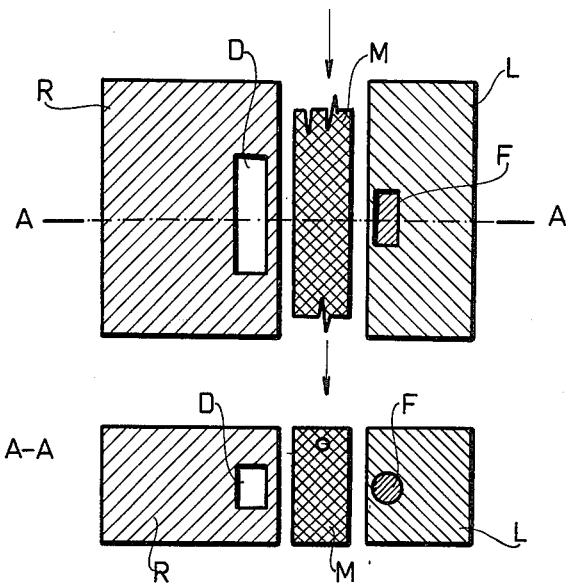
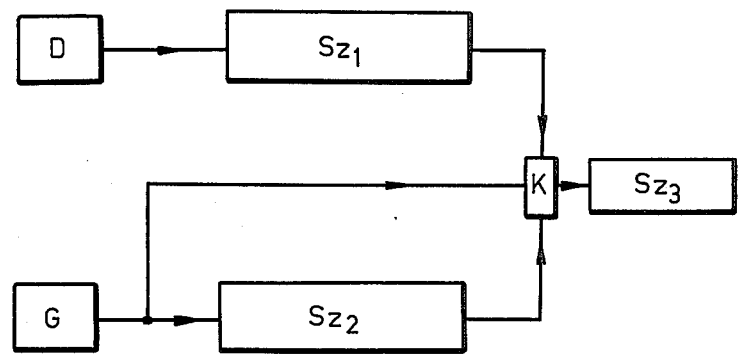
Fig.1
Fig.2

MEASURING THE CONCENTRATION OF BORON IN WATER

This application is a continuation-in-part of our copending application Ser. No. 520,143, filed Nov. 1, 1974, and now abandoned.

Boron has become, by virtue of its contained isotope $10_B$ having high neutron absorbing capacity, an important reactor physical and technical substance. It is in wide spread use as material for control rods in the form of boroncarbide.

The importance of boron in nuclear power stations having pressurized water reactors increased in recent years abruptly the use of the so-called chemical control. In this method of control boron - in natural or enriched in $10_B$ state —is dissolved in the form of boric acid in the cooling water of the reactor, and the absorbing capability is ensured by control of concentration. The most important advantages of chemical control in comparison to the control rod methods are:

the thermal neutron flux is made more even so that the power to be drawn off from reactors having equal geometry, dimensions and technological limits increased;

in case of its use control rods and controlling devices fewer in number are necessary, by which the starting reactivity to be built in, may be increased;

as a result the burning out level of reactors, and the time elapsing between fuel changes might be increased.

It is beyond doubt that introducing the above method will have a decisive economical advantage.

Boric acid control necessitated new dosing, discharging, cleaning, etc. devices to be constructed, and continuous measurement of boron concentration has been made necessary too. Boron concentration measurement by some traditional method, as e.g. by titrometry, is generally periodical, complex, and lengthy, therefore a method suiting better the purpose had to be sought.

For the continuous measurement of boron concentration, research started in different places and was based on different methods. The methods are belonging basically to two groups, namely:

chemical and isotope methods.

With chemical methods the problem may be solved either periodically (K. Schneider: Automatic Boron Analysator to Pressurized Reactors. Nuclex 72 Ch-4021, Basel, Switzerland), or with a very great delay only. The literature: J. E. Bulkowski, W. D. Fletcher, A. G. Opitz, V. Bajagopal: Development of a Boron Concentration Measuring Apparatus; Final Report. AEC Contract T/30 — 1/-3690. April 1969 deals in detail with measuring equipment based on conductivity measurement. The boron analyzer of Schneider deals with semi-periodical titri-pH measuring equipment, while Fahrmann and Japel disclose a patented measuring cell using an isotope. (K. Fahrmann, F. Jape: Measuring Device for the Control of Boric Acid Concentration in Reactors, Kernenergle 1967/11).

The research report prepared by Westinghouse Electric Co. Laboratories (Bulkowski et al.) relates to a boric acid concentration measuring apparatus based on the conductivity of mannite, and reports also on the apparatus of Bajagopal based on neutron absorption. From the two devices, based on service experiences and cost estimates, the apparatus of Bajagopal has been held more suitable.

Summarizing the results obtained up to now, it may be concluded, that concerning costs and labor utilization, significant researches are going on. Nevertheless in spite of these no equipment suitable for mass production has been made. An instrument having linear character has been developed up to 5 g/kg concentration only.

Measuring and control requirements regarding power reactors or nuclear power stations are in many respects more severe, because of extraordinary conditions prevailing at measuring sites, as those customary in nuclear measuring equipment, working under laboratory or normal service conditions.

The present invention relates to a boron concentration measuring set-up too. For an adequate solution of the problem, as for utilization of the advantages of the method used by us, the apparatus ought to be built into the primary cooling circuit of the reactor. Because of the high pressure and temperature prevailing in the primary circuit, and because of the strong radioactive radiation, special requirements are to be met, primarily by the vessel containing the liquid to be measured, and by the detecting system. The measuring equipment meeting the requirements has to be as simple and as cheap as possible.

In the accompanying drawings:

FIG. 1 is a somewhat schematic cross-sectional view of apparatus for practicing a method according to the invention; and FIG. 2 is a simplified circuit diagram of the invention;

The radioactive neutron source F is contained within the vessel L filled with a neutron moderator substance (water, paraffin, etc.) in the arrangement shown in FIG. 1. The neutrons streaming from vessel L in the direction of the proportional radiation detector (neutron detector) filled at D with boron trifluoride gas, are absorbed by boron, or another neutron absorbing substance according to the concentration in the measuring vessel M surrounded by surfaces comprising at least two mutually parallel planes.

By expedient choice of the material and dimensions of the high pressure resistant vessel M and moderator L and reflector R as well, moreover by the relative arrangement of the measuring vessel M, moderator L, reflector R, radiation source F, and detector D, it can be achieved that the relation between the concentration of water dissolved boron (or other neutron absorbing substance) and the time of measurement necessary to reach a given (arbitrary) detector pulse number N, shall be linear.

Neutron reflector R (e.g. graphite) reflects the neutrons passed by detector D, and thus increases the effectiveness of measurement, and enables one to use less intensive neutron sources, which in turn reduce the hazards and lower production costs.

By the measuring set-up disclosed above it has been possible to achieve, that the relation between the time necessary for gathering up the given amount N of pulses, and the boron concentration should be linear.

If $T_o$ is the time necessary for collecting N pulses in case of pure water, and $T_1$ the time in case of a solution containing boric acid in $C_1$ g/kg concentration, and $\Delta T_o$ the difference in time between the above two, chosen by us, the following equations may be written:

$(T_1/T_o) = K$ $T_1 - T_o = \Delta T_o$ where $K$ is a constant characterisitc to the apparatus. From these $T_o$ and $T_1$ may be expressed:

$$T_o = (\Delta T_o)/(K - 1)$$

$$T_1 = K/(K - 1) \Delta T_o$$

Preset counter $Sz_1$ of the apparatus counts the signals coming from the detector and stops the measurement upon reaching the prescribed pulse number N. Display counter $Sz_3$ counts through a conventional gate K the signals of the time base generator G, but only from the moment $t = T_o$, i.e. when the output signal of time preset counter $Sz_2$ opens gate K. The condition for opening gate K is determined commonly by counters $Sz_1$ and $Sz_2$. The apparatus substracts in this way automatically the time of measurement pertaining to zero boric acid concentration, i.e. measures directly the value $\Delta T = T - T_o = B.C$, where again B is a constant characteristic of the equipment.

Signals from generator G, counted by display counter $Sz_3$, are stopped at gate K by the inhibit output signal of preset counter $Sz_1$ when the number of pulses from detector D reaches the value that was preset on $Sz_1$.

Thus display counter $Sz_3$ counts through gate K the signals of the time base generator G, but only from the moment $t = T_o$, that is, when the output signal of time preset counter $Sz_2$ opens gate K. Signals from generator G, counted by display counter $Sz_3$ are stopped at gate K by the inhibit output signal of preset counter $sz_1$ when the number of pulses from detector D reaches the value that was preset on $Sz_1$.

Let it be assumed that, for example, 1,000 pulses are received by detector D in 10 seconds when the specimen between neutron source F and detector D is pure water.

If instead of pure water, a boron-containing solution is present, then there will be a greater adsorption of neutrons by the test specimen, and 1,000 pulses will not be received in 10 seconds, but instead a lesser number of pulses will be received in 10 seconds. Stated the other way, 1,000 pulses will then be received in a period of time greater than 10 seconds. Let it be assumed that the boron concentration is such that this greater period of time is, say, 15 seconds.

When time base generator G and pulse detector D start to function at the beginning of a test, therefore, gate K is closed. Time preset counter $Sz_2$ is set for 10 seconds; while pulse preset counter $Sz_1$ is set for 1,000 pulses. After 10 seconds has elapsed, time preset counter $Sz_2$ opens gate K, after which the signals from time base generator G register on display counter $Sz_3$. At this point, however, pulse preset counter $Sz_1$ has detected only, say 670 pulses. The signals from generator G continue to register on display counter $Sz_3$ for an additional 5 seconds, until pulse preset counter $Sz_1$ has counted its 1,000 pulses, after which $Sz_1$ closes gate K and the display on counter $Sz_3$ stops changing, for a display corresponding to 5 seconds, which, of course, will be displayed in terms of the boron concentration that produces the degree of neutron adsorption that has lengthened $T_o$ from 10 seconds to $T_1$ of 15 seconds.

Although the present invention has been described and illustrated in connection with preferred embodiments, it is to be understood that modifications and variations may be resorted to without departing from the spirit of the invention, as those skilled in this art will readily understand. Such modifications and variations are considered to be within the purview and scope of the present invention as defined by the appended claim.

What we claim is:

1. Method for the determination of the concentration of boron in water, comprising establishing a measuring vessel bounded on opposite sides by flat surfaces that are parallel to each other, introducing into said vessel between said surfaces an aqueous solution containing boron, establishing a radio-active neutron source on one side of said vessel in a neutron moderator, positioning a neutron detector in a neutron reflector on the other side of said vessel from said neutron source, the path between said source and detector being perpendicular to said surfaces, measuring the time during which a predetermined quantity of neutrons are received by said detector, comparing the measured time with a known time required for the receipt by said detector of the same said predetermined quantity of neutrons when said vessel contains pure water, and displaying the concentration of said boron as a function of said measured time which is in the excess of said known time.

* * * * *